United States Patent [19]
Sanberg et al.

[11] Patent Number: 6,036,951
[45] Date of Patent: *Mar. 14, 2000

[54] SERTOLI CELLS AS NEURORECOVERY INDUCING CELLS FOR NEURODEGENERATIVE DISORDERS

[75] Inventors: Paul R. Sanberg, Springhill; Don F. Cameron; Cesario V. Borlongan, both of Lutz, all of Fla.

[73] Assignee: University of South Florida, Tampa, Fla.

[ * ] Notice: This patent is subject to a terminal disclaimer.

[21] Appl. No.: 08/913,865

[22] PCT Filed: Mar. 12, 1996

[86] PCT No.: PCT/US96/03335

§ 371 Date: Sep. 12, 1997

§ 102(e) Date: Sep. 12, 1997

[87] PCT Pub. No.: WO96/28030

PCT Pub. Date: Sep. 19, 1996

[51] Int. Cl.[7] .......................... A61K 48/00; A61K 35/00; C12N 15/85
[52] U.S. Cl. ...................... 424/93.1; 424/93.21; 435/325
[58] Field of Search ............................ 424/93.1; 435/325

[56] References Cited

PUBLICATIONS

Willing et al. (Nov. 1998) Mol. Med. Today, vol 4(11), 471–477.
Sanberg et al. (Dec. 1996) Nat. Biotech., vol. 14, 1692–1695.
Greenstein et al. (Mar. 1997) Nat. Biotech., vol. 15, 235–238.
Haque et al. (Apr. 1997) Mol. Med. Today, vol. 3 (4), 175–183.
Gao et al. (Apr. 1997) Exp. Opin. Ther. Pat., vol. 7 (4), 325–338.
M.D. Griswold (1992) The Sertoli Cell, Cacher River Press, Russel, L.D., and Griswold, M.D. eds., 195–200.
Bjorklunc and Stenevi, "Intracerebral neural grafting: a historical perspective" in Bjorklund, A and U. Stenevi, eds. *Neural grafting in the mammalian CNS*, Amsterdam: Elsevier, 3–11 (1985).
Bjorklund, "Dopaminergic transplants in experimental Parkinsonism: Cellular mechanisms of graft–induced functional recovery" *Current Biology*, 2:683–689 (1992).
Borlongan et al., "PR: Systemic 3–nitropropionic acid: Behavior deficits and striatal damage in rats" *Brain Research Bulletin*, 36:549–556 (1995).
Cameron et al., "Successful islet/abdominal testis transplantation does not require Leydig cells" *Transplantation*, 50:549–556 (1995).
Cameron and Muffly, "Hormonal regulation of spermatid binding to Sertoli cells in vitro." *J. Cell Sci.*, 100:523–533 (1991).
Carson et al., "Synthesis and Secretion of a Novel Binding Protein for Retinol by a Cell Line Derived from Sertoli Cells" *Journal of Biological Chemistry*, 259:3117–3123 (1964).
Griswold, "Protein Secretion by Sertoli cells: general considerations" in Russell, L.d. and M.D. Griswold eds. The Sertoli Cell, Cache River Press, Clearwater, FL, 195–200 (1992).
Isacson et al., "Graft–induced behavioral recovery in an animal model of Huntington's disease" *Proc. Natl. Acad. Sci.*, 83:2728–2732 (1986).
Koutouzis et al., "PR:Systematic 3–nitropropionic acid: Long term effects on locomotor behavior" *Brain Research*, 646:242–246 (1994).
Lindvall et al., "Transplantation in Parkinson's disease: two cases of adrenal medullary grafts to the putamen" *Ann. Neurol.* 22:457–468 (1987).
Lindvall et al., "Grafts of fetal dopamine neurons survive and improve motor function in Parkinson's disease" *Science*, 247:574–577 (1990).
Pakzaban et al., "Increased proportion of Ache–rich zones and improved morphological integration in host striatum of fetal grafts derived from the lateral but not the medial ganglionic eminence" *Exp. Brain Res.*, 97:13–22 (1993).
Sanberg et al., "Cell transplantation for Huntington's disease" R.G. Landes Co., Boca Raton, FL, pp. 19–21 (1994). [n/a—will mail in].
Sanberg et al., "Testis–derived Sertoli cells have a trophic effect on dopamine neurons and alleviate hemiparkinsonism in rats" *Nature Medicine*, 3:1129–1132 (1997).
Selawry and Cameron, "Sertoli cell–enriched fractions in successful islet cell transplantation" *Cell Transplant*, 2:123–129 (1993).
Wictorin et al., "Reformation of long axon pathways in adult rat CNS by human forebrain neuroblasts" *Nature*, 347:556–558 (1990).

*Primary Examiner*—Scott D. Priebe
*Assistant Examiner*—Anne Marie S. Beckerleg
*Attorney, Agent, or Firm*—Kohn & Associates

[57] ABSTRACT

A method of generating in situ trophic factor production by transplanting Sertoli cells into a tissue in need of trophic factors of a mammal, the cells creating trophic factors in situ.

4 Claims, 4 Drawing Sheets

SERTOLI CELLS AS NEURORECOVERY INDUCING CELLS FOR NEURODEGENERATIVE DISORDERS

TECHNICAL FIELD

The present invention generally relates to cell transplantation and specifically to a method of transplanting cells which, following transplantation into the central nervous system (CNS), ameliorates the behavioral and functional deficits associated with neurological and neurodegenerative disorders.

BACKGROUND OF THE INVENTION

In treating disease it is often useful to treat tissue locally, rather than systemically, with trophic factors, particularly areas of tissue damage as for example in wound healing.

As a further example, transplantation of neural tissue into the mammalian central nervous system (CNS) is becoming an alternative treatment for neurological and neurodegenerative disorders including epilepsy, stroke, Huntington's diseases, head injury, spinal injury, pain, Parkinson's disease, myelin deficiencies, neuromuscular disorders, neurological pain, amyotrophic. lateral sclerosis, Alzheimer's disease, and affective disorders of the brain. Preclinical and clinical data indicate that transplanted cells (the graft) used in cell transplantation protocols for these types of neurodegenerative diseases survive and integrate with the host tissue, and provides functional recovery. (Sanberg et al., 1994).

The primary source for these grafts has been the fetus. For example, fetal ventral mesencephalic tissue has been demonstrated to be a viable graft source in Parkinson's disease. (Lindvall et al., 1990; Bjorklund, 1992). Likewise, fetal striatal tissue has been utilized successfully as graft material in Huntington's disease. (Isacson et al., 1986; Sanberg et al., 1994).

Neurologically dysfunctional animals have been transplanted with non-fetal cells and non-neuronal cells/tissue. For example, chromaffin cells from adult donors have been used in the treatment of Parkinson's disease. The major advantage of this type of transplantation protocol is that the graft source is not a fetal source and, thereby, circumvents the ethical and logistical problems associated with acquiring fetal tissue. Utilizing the chromaffin cell protocol, normalization of behavior is observed. However, the functional recovery of this behavior is temporary and the animals revert to their pre-transplantation status (Bjorklund and Stenevi, 1985; Lindvall et al., 1987). The inability of this type of treatment protocol to maintain normal behavioral activity in animals in the Parkinson's disease model renders clinical application of this protocol as well as other treatment therapies premature.

Administration of growth factors as a means of treating neurological and neurodegenerative diseases has been contemplated in the art. However, delivering these agents to the brain is fraught with great difficulties that have yet to be successfully overcome. Generally, these agents cannot be administered systemically and infusion into the brain is an impractical and imperfect solution. Engineering cells to deliver specific, single trophic factors when implanted in the brain has been suggested, but stable transfection and survival of the cells when implanted in the brain continues to be problematic. Additionally, it is becoming increasingly recognized that multiple trophic factors acting in concert are likely to be necessary for the successful treatment of neurological and neurodegenerative conditions.

Long term maintenance of functional recovery has been observed in a diabetic animal model utilizing a novel transplantation treatment protocol utilizing isolated islet cells and Sertoli cells. It is clear that the efficacy of the treatment is due to the presence of the Sertoli cells, in part, due to their known immunosuppressive secretory factor. (Selawry and Cameron, 1993; Cameron et al., 1990). Sertoli cells are also known to secrete a number of important trophic growth factors.

Accordingly, it would be desirable to utilize Sertoli cells alone as a source for diseases where growth and trophic factor support of damaged tissue is useful. Examples include, wound healing and neurological disorders including neurodegenerative disorders. The Sertoli cells can be used to function as an in situ factory for trophic factors to thereby hasten wound healing and to ameliorate functional and behavioral deficits associated with neurological and neurodegenerative disorders.

SUMMARY OF THE INVENTION

In accordance with the present invention, there is provided a method of generating in situ trophic factor production by transplanting Sertoli cells into a mammal, the cells secreting trophic factors in situ.

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE INVENTION

Figure 1:
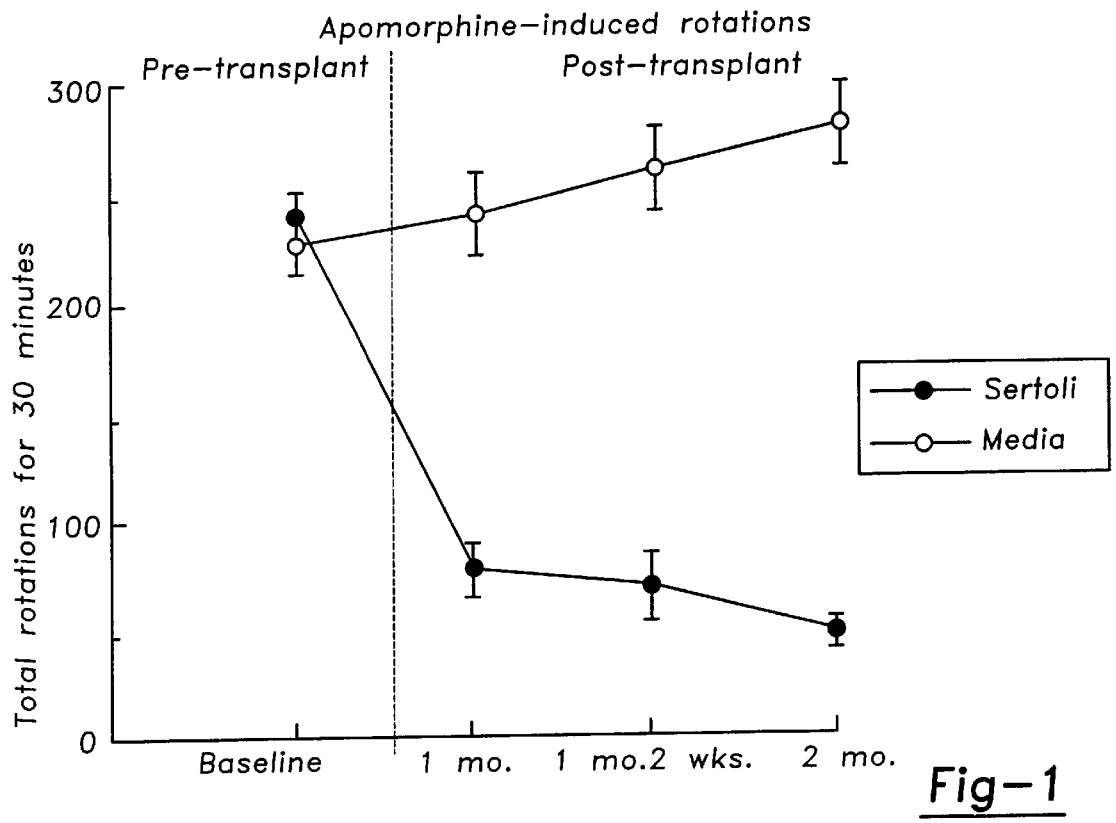
FIG. 1 is a graph showing the results of apomorphine-induced rotational behavior, animals from both groups exhibited >7 rotations per minute or, at least, a total of 210 rotations for 30 minutes (contralateral to the lesion) when challenged with apomorphine pre-transplant, at post-transplant periods, animals receiving media alone continued to display significant rotations, in contrast, animals receiving the Sertoli cells had a marked reductions (more than 600a) in their rotational behavior across the post-transplant periods.

Generally, the present invention provides a method for promoting the repair, protection, and support of dysfunctional tissue by mechanisms including in situ production of Sertoli cell-derived growth and regulatory factors referred to generally as trophic factors. Additionally, the present method provides a method of generating in situ trophic factor production. This is achieved by transplanting isolated Sertoli cells into a mammal, the cells secreting trophic factors in situ.

One significant benefit of utilizing Sertoli cells as an in situ factory for producing trophic factors is that Sertoli cells have been shown to have an effective immunosuppressant effect. Accordingly, concomitant adjunctive therapy to produce immunosuppression is not required. In other words, the Sertoli cells can be used as a trophic factor source while also providing a self-induced local immunosuppressive effect.

Trophic factors secreted by Sertoli cells include Sertoli cell-derived growth and regulatory factors such as insulin-like growth factors I and II, epidermal growth factor, transforming growth factors α and β, and interleukin 1α (Griswold, 1992). For a more extensive list of Sertoli cell secretory factors refer to Table 1. Such factors have been shown to have an ameliorative effect on behavioral and functional deficits associated with neurodegenerative diseases. These factors are well known tropic factors which support normal cell and tissue metabolism and function. (Griswold, 1992). The present invention utilized the phenomenon that Sertoli cells can produce a trophic-rich, growth-supportive fluid microenvironment at the site of cellular dysfunction or cellular/tissue damage. Cellular/tissue damage can include, but is not limited to, radiation damage, burns and wounds. In contrast to the Sertoli cell/islet cell transplantation protocol used in the diabetic model, the method of the present invention utilizes only one type of cell, i.e. Sertoli cells, thereby significantly reducing the logistic and procedural problems inherent in attempting to transplant two different cell types at one host site.

Although rat Sertoli cells are utilized in the following examples, Sertoli cells from any suitable source can be used. For example, human Sertoli cells may be used for transplantation in humans. Additionally, in a preferred embodiment of the present invention, porcine Sertoli cells may be transplanted into a mammal, such as a human. Furthermore, veterinary uses of the present invention are contemplated and allogenic Sertoli cells would be selected for transplantation into the desired mammalian host.

As demonstrated in the experimental section below, the present invention can be utilized as a treatment for ameliorating the behavioral and functional deficits associated with neurodegenerative diseases, such as Huntington's disease and Parkinson's disease. This can be accomplished without the concomitant side effects of previously utilized immunosuppressive adjuvant therapy, such as the chronic use of cyclosporine A. The Sertoli cells, to provide both the secretion of the trophic factors and the immunosuppressive effect.

As shown in the examples below, the transplantation of Sertoli cells prior to inducing or formation of a brain lesion can provide a neuroprotective effect. For example, as demonstrated below, implantation of Sertoli cells prior to inducement of a Huntington's type disease provided both neuroprotective and prophylactic effects on a subsequent brain lesion. Therefore, the implantation of Sertoli cells early on following diagnosis of a neurodegenerative disease may provide useful treatment, prevention or reduction of the disease. Additionally, Sertoli cells may be transplanted in other types of CNS trauma such as head injury to treat, prevent, and/or prophylactically reduce the effects of CNS injury.

The following example demonstrates the ability of the present invention to ameliorate behavioral deficits associated with neurodegenerative disorders.

EXAMPLE 1

SERTOLI CELL TRANSPLANTATION

Specific Protocol:

The protocol generally involves two basic steps, (1) Sertoli cell isolation and (2) cell transplantation both of which are briefly described below (for greater details regarding the cell isolation see Selawry and Cameron (1993) and for details regarding cell transplantation, see Pakzaban et al.(1993) both incorporated by reference.

(1A) Sertoli Cell Isolation

The isolation procedure follows a well defined method Selawry and Cameron, (1993) and is routinely utilized. The cell culture medium used in all isolation steps and in which the cells were incubated was DMEM:Hams F12 supplemented with retinol, ITS, and gentamicin sulfate (Cameron and Muffly, 1991). Testes were surgically collected from sixteen day old male Sprague-Dawley rats. The testes were decapsulated and prepared for enzymatic digestion to separate other testicular cell types from the Sertoli cells. The enzymatic procedure utilized collagenase (0.1%), hyaluronidase (0.1%), and trypsin (0.25%) which is a typical procedure used in many cell isolation protocols. After sequential enzymatic digestion, the Sertoli cell isolate was washed with culture medium, transferred to sterile culture vessels and placed in a humidified, 5% $CO_2$-95% air tissue culture incubator. Following forty-eight hours of pre-incubation in a 39° C. incubator, the Sertoli cells were washed to remove any contaminating debris. The resultant Sertoli cell-enriched fraction was resuspended into 0.25 ml of DMEM/F12 medium and incubated at 37° C. for at least 24 hours.

The Sertoli cells are then liberated from the vessel floor with trypsin, transferred to a sterile conical test tube, and repeatedly washed by centrifugation and treated with trypsin inhibitor to cease the enzymatic action of the trypsin. During the day of transplantation, the Sertoli cell-enriched fraction is resuspended and suctioned using a Hamilton syringe with a 20 gauge spinal needle.

(1B) Isolation and Pretreatment of Sertoli Cells

Alternatively, as previously described (Cameron et al. 1987a; Cameron et al. 1987b) decapsulated rat testes were subjected to sequential enzymatic treatment at 37° C. using 0.25% trypsin (Sigma) and 0.1% collagenase (Sigma, type V) (Cameron et al. 1987a; Cameron et al. 1987b). The resulting Sertoli cell aggregates were equally distributed in a volume of 20 ml incubation medium into 75 cm² tissue culture flasks (Costar). Plated Sertoli aggregates were incubated at 39° C. in 5% $CO_2$-95% air for 48 hours after which cells were subjected to hypotonic treatment with sterile 0.5 mM Tris-Hcl buffer for one minute (Galdieri et al. 1981) to expedite the removal of contaminating germ cells. Following two washes with incubation medium, flasks were replenished with 20 ml incubation medium and returned to the $CO_2$-injected incubator at 37° C. in 5% $CO_2$-95% air. The resulting pre-treated Sertoli-enriched monocultures contained greater than 95% Sertoli cells. Plating density (<2.0× $10^6$ Sertoli cells/cm²) did not result in a confluent monolayer of cells.

(2) Cell Transplantation

Figure 5A:
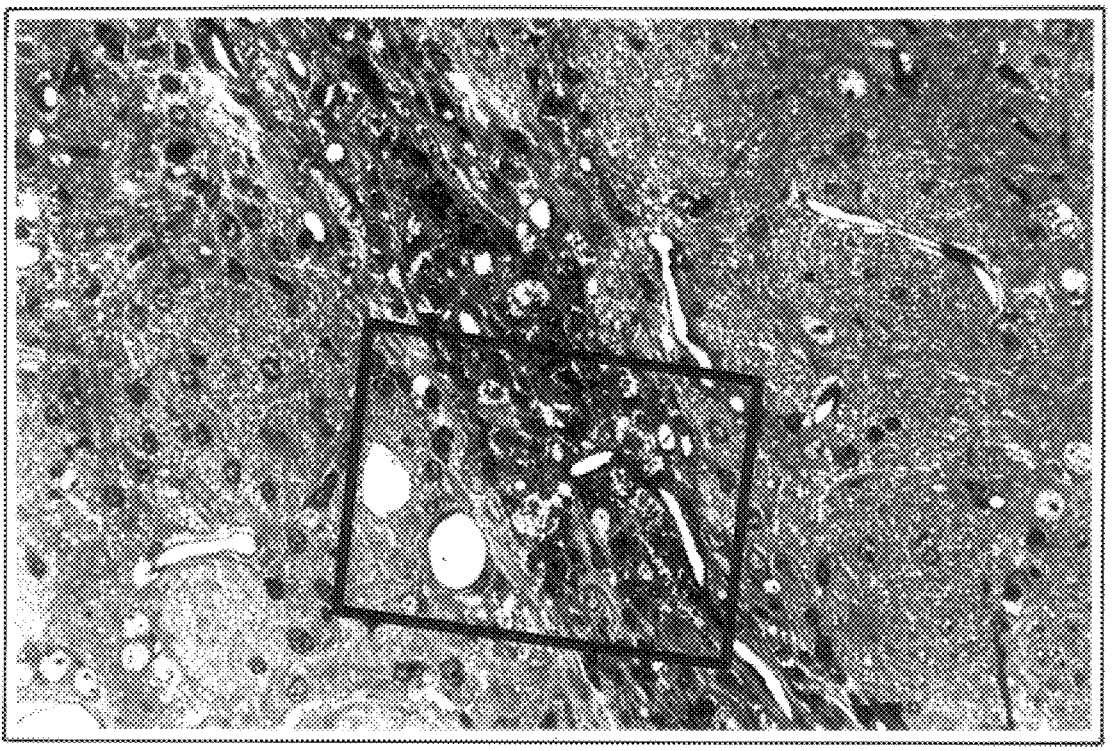
FIGS. 5A–B are two light micrographs illustrating grafted Sertoli cells in situ labeled with a florescent tag (DiI) prior to their transplantation into the striatum of the brain wherein (A) depicts viable, florescent Sertoli cells in a rat host that had not received immunosuppression therapy with cyclosporine A (CsA), and (B) shows viable, florescent Sertoli cells in the rat host that had received cyclosporine A immunosuppression therapy.
Figure 5B:
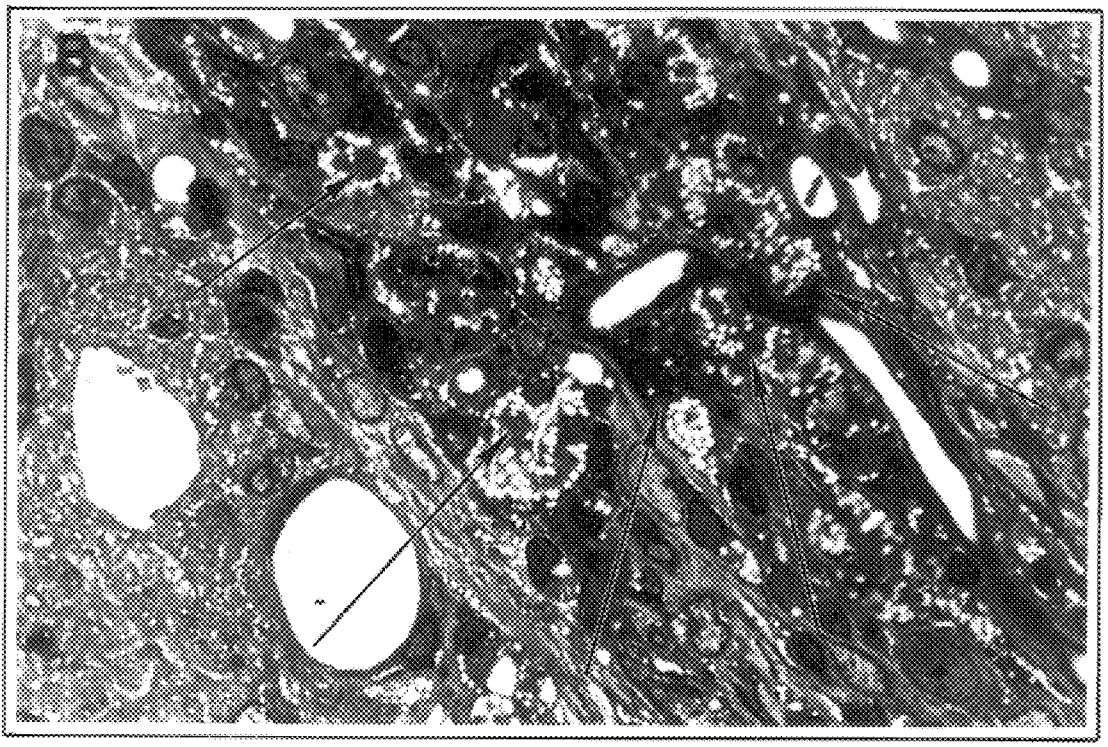

The transplantation protocol follows the procedure as previously described (Pakzaban et al., 1993). Animal surgery was carried out under sterile conditions. All animals were initially anesthetized with 0.60 ml/kg sodium pentobarbital and then were placed in a Koph stereotaxic instrument. Unilateral striatal transplants were performed using coordinates set at: anteroposterior=+1.2, mediolateral=+/−2.8, dorsoventral=6.0, 5.9, and 5.8 (based on the atlas of Paxinos and Watson, 1984). The striatum ipsilateral to the lesioned substantia nigra was transplanted with Sertoli cells. Each striatum receives a total volume of 3 µl of Sertoli cell suspension. One microliter of the Sertoli cell suspension was infused over one minute per dorsoventral site. Controls only received media. Another five minutes was allowed upon reaching the last dorsoventral site before retracting the needle. After surgery, the animals were placed on heating pads to recover. Animals receive a short course of immunosuppression using Cyclosporine-A (20 mg/kg/d, i.p.) immediately after surgery and on the day following transplant. However, subsequent studies demonstrated that this short course of Cyclosporine-A is not needed (FIGS. 5A–B)

Sertoli cells are transplanted into animal models of various neurodegenerative disorders by stereotaxic coordinates defined for the specific disorder, as illustrated in the Parkinson's disease example, and then are systemically assayed for functional recovery by techniques specific to that animal model.

The present study used Sprague-Dawley male, eight week old rats with 6-OHDA-induced hemiparkinsonism (n=12). At three weeks post-lesion, the animals were subjected to behavioral tests that included the apomorphine-induced rotational behavior and the swing behavior. Baseline data showed significant apomorphine-induced rotational behavior (contralateral to the lesioned side of the CNS) in all these animals (at least 200 turns for 30 minutes). Using the elevated body swing test (EBST), significant right-biased swing activity (more than 70%) was also noted.

At three weeks post-lesion, one group of animals (n=6) received Sertoli cells and one group (n=6) was subjected to the same surgical procedure but only received media (DMEM without serum) as controls. All animals received cyclosporine (20 mg/kg) for the first two days following the transplant. At one, one and a half, and two months post-transplant, animals were again introduced in the same behavioral tests.

Figure 2:
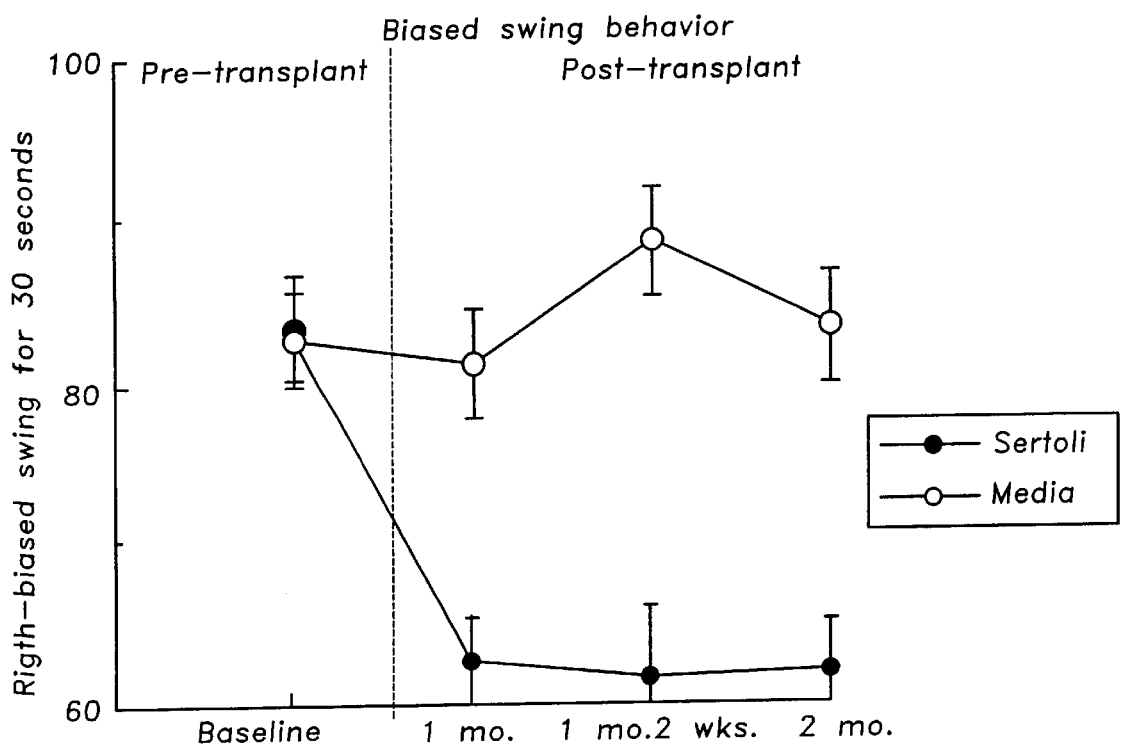
FIG. 2 is a graph showing biased swing behavior, animals from both groups displayed >80% biased swing activity (contralateral to the lesion) as revealed by the elevated body swing test, at post-transplant periods, animals receiving the media alone continued to display significant biased swing activity, in contrast, animals receiving the Sertoli cells did not exhibit any biased swing behavior across the post-transplant periods.

The animals receiving Sertoli cells exhibited significant reductions in rotations (mean of 50 turns for 30 minutes) while the animals receiving the media alone were at pre-transplant rotational level (FIG. 1). The normalization of turning behavior persisted across the two month test period. The right-biased swing activity previously displayed by the Sertoli cells transplanted animals was also significantly reduced at post-transplant test sessions (FIG. 2). The animals receiving the media did not show any significant reductions in their right-biased swing responses.

At autopsy, brains were removed from the animals and fixed for vibratome sectioning at 40–80 µm. Following staining, there was a marked reduction of activated glial cells at the penetration site (i.e., lesion site) in Sertoli cell transplanted rats when compared to the penetration site in the lesioned animals not transplanted with Sertoli cells.

EXAMPLE 2

GROWTH OF NEURAL CELLS

Incubation Medium and Sertoli Cell Pre-conditioned Medium

The incubation medium used for Sertoli cell culture and co-culture was Dulbecco's Minimum Essential Medium-:Hams F12 Nutrient Medium (Whittaker Bioproducts) mixed 1:1 and supplemented with 3 mg/ml L-glutamine (Sigma, grade III), 0.01 cc/ml insulin-transferrin-selenium (ITS, Collaborative Research, Inc.), 50 ng/ml retinol (Sigma), 19 µl/ml lactic acid (Sigma) and 0.01 cc/ml gentamicin sulfate (Gibco).

Following the first 48 hour incubation period of isolated Sertoli cells, media was collected and centrifuged at 1500 rpm for 5 minutes. The supernatant was collected and immediately frozen in sterile test tubes. This medium was identified as Sertoli pre-conditioned medium (SCM).

Isolation and Incubation of Fetal Brain Cells

Fetal brain cells (FBC) were collected from the ventral mesencephalon of fetal rats (15–17 days gestation). The fetal brain tissue was suspended in medium and initially dispersed by passing it through a series of sequentially decreasing sized hypodermic needles (18–26 gauge). The resulting suspension was treated with 0.1% trypsin for five minutes and followed by 0.1% trypsin inhibitor for two minutes. The suspended FBC were washed (3×), resuspended in incubation medium and plated in poly-L-lysine-coated culture vessels.

Figure 3A:
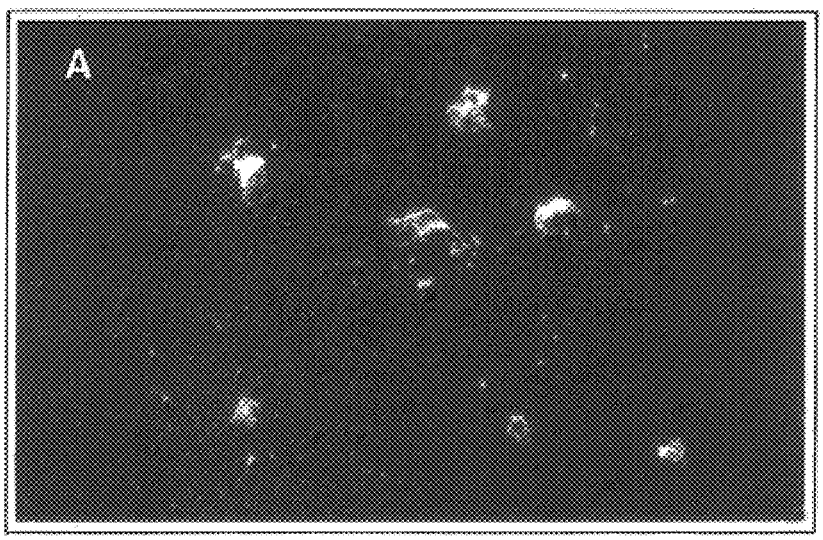
FIGS. 3A–C are light micrographs illustrating cells from the ventral mesencephalon of fetal rats (VM) isolated and cultured for seven days in control medium (CM) or Sertoli cell pre-conditioned medium (SCM) and photographed with darkfield, interference contrast optics, wherein (A) depicts VM cells incubated in CM showing no evidence of stimulation or differentiation, (B) depicts VM cells incubated in SCM appearing highly stimulated, and (C) at higher magnification, depicts VM cells incubated in SCM exhibiting neurite outgrowth as a result of Sertoli secreted trophic factors.
Figure 3B:
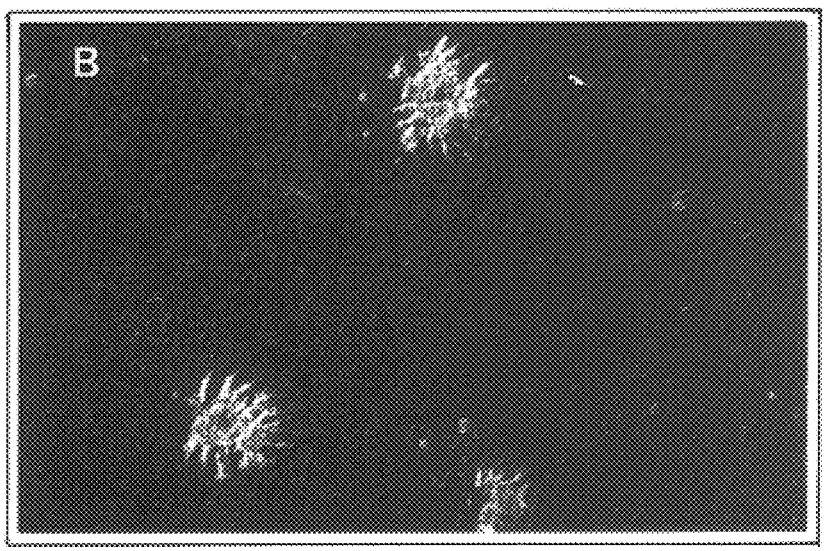
Figure 3C:
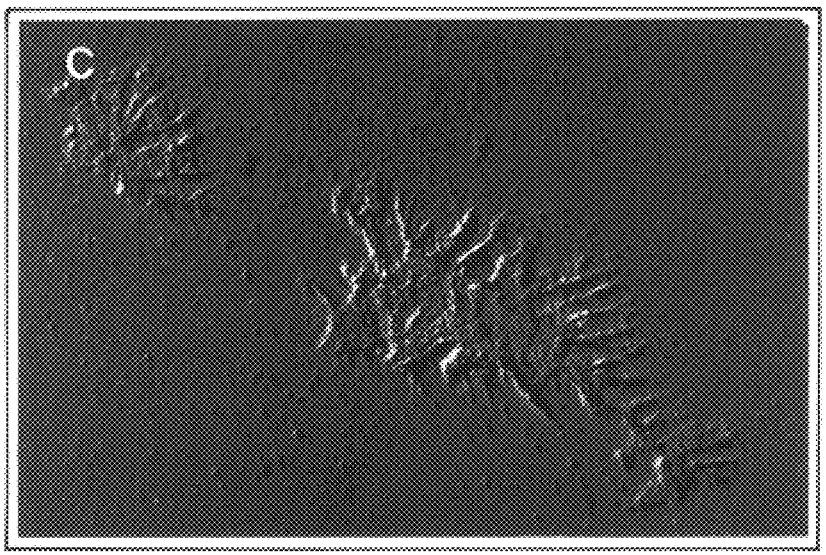

Cells from the ventral mesencephalon of fetal rats (VM) were isolated and cultured for seven days in control medium (CM) or Sertoli cell pre-conditioned medium (SCM) as shown in FIG. 3A. VM cells incubated in CM showed no evidence of cellular stimulation or differentiation. Referring to FIG. 3B, VM cells incubated in SCM were highly stimulated. FIG. 3C illustrates that at higher magnification, VM cells incubated in SCM show neurite outgrowth as a response to Sertoli cell secreted trophic factors.

EXAMPLE 3

IDENTIFICATION OF SERTOLI CELLS

Incorporation of Latex Beads:

Sertoli cells were isolated and prepared for incubation as described. Prior to transplantation (approximately 12 hours), sterile laim latex beads (10 µl/ml medium; Pelco, Tustin, Calif.) were added to the incubation medium. Sertoli cells rapidly phagocytosed the beads. Immediately prior to transplantation, the beaded Sertoli cells were washed (three times) and resuspended in 1ml of incubation medium.

Figure 4A:
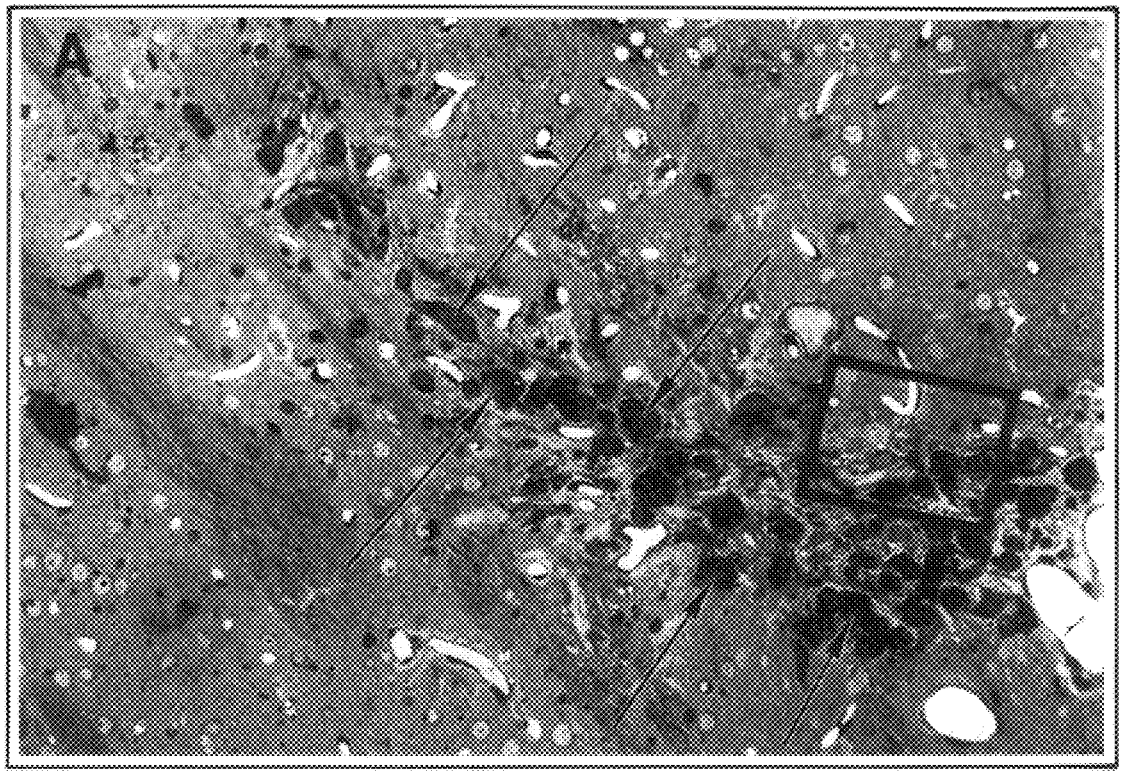
FIGS. 4A–B are electron micrographs illustrating (A) the striatum of the brain showing the penetration tract (arrows) and the site of Sertoli cell transplantation, and (B) shows the boxed area in (A) at higher magnification, with higher resolution, Sertoli cells (arrows) are easily identified because of the 1μ latex bead inclusions which were loaded into the cells prior to transplantation.
Figure 4B:
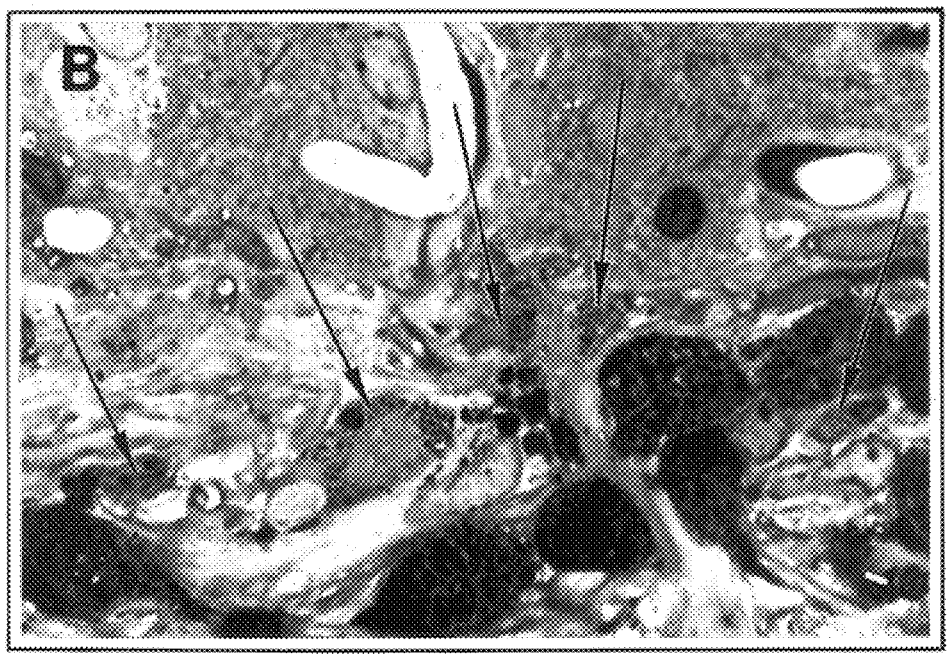

Referring to FIG. 4A, Sertoli cells were transplanted into the striatum of the brain wherein the penetration tract (arrows) and the site of Sertoli cell transplantation are shown. At higher magnification as shown in FIG. 4B, Sertoli cells (arrows) were easily identified because of the inclusion of 1µ latex beads which were loaded into the Sertoli cells prior to transplantation.

EXAMPLE 4

EFFECTS OF CYCLOSPORINE A (CSA) ON THE SURVIVAL OF TRANSPLANTED SERTOLI CELLS

Fluorescent Cell Labeling:

Immediately prior to transplantation (approximately two hours), Sertoli cell monocultures were treated with CM-DiI fluorescent dye for cell tracking (100 μl stock/ml medium; Molecular Probes, Inc., Eugene, Oreg.) for seven minutes at 37° C. and then placed at 4° C. for an additional 15 minutes. Fluorescent "tagged" Sertoli cells were washed (3x) and resuspended in 1 ml of incubation medium.

The effect of cyclosporine A on the survival of grafted Sertoli cells in situ was examined. Grafted Sertoli cells were labeled with a fluorescent tag (DiI) prior to transplantation into the striatum of the brain. The tissue was collected one month post-transplantation. Referring to FIG. 5A, viable fluorescent Sertoli cells were seen in a rat host that had not received immunosuppression therapy with cyclosporine A. Referring to FIG. 5B, viable fluorescent Sertoli cells are shown in a rat host that had received cyclosporine A immunosuppression therapy. This example demonstrates that cyclosporine A is not necessary for the survival of Sertoli cells transplanted into the brain.

EXAMPLE 5

PROPHYLACTIC EFFECTS OF SERTOLI CELLS

The transplantation of Sertoli cells is neuroprotective when implanted prior to inducing brain lesions. This prophylactic effect of Sertoli cells was demonstrated in an animal model for Huntington's Disease (HD). This model is produced by the systemic administration of the mitochondrial inhibitor, 3-nitropropronic acid (3NP). It has been demonstrated by Sanberg and colleagues (Koutouzis et al. 1994; Borlongan et al. 1995) and others that the injection of 3NP causes specific lesions within the striatum which mimic the pathology seen in Huntington's disease.

In the present experiment 8 rats were transplanted with rat Sertoli cells (as described previously) unilaterally into one striatum of normal rats. Therefore, one side of the brain had Sertoli cells and the other side was without. One month later, the animals were injected with 3NP as described elsewhere (Koutouzis et al. 1994; Borlongan et al. 1995) to induce HD. Normal rats when injected with 3NP demonstrate bilateral damage of the striatum of the brain and have behavioral deficits which are equal on both sides of the body (Koutouzis et al. 1994; Borlongan et la. 1995).

One month following 3NP administration the animals demonstrated unilateral behavioral deficits. This was seen by the demonstration of apomorphine-induced rotations post-lesion in Sertoli transplanted animals, but not in controls (Number of Rotations; Controls=0.25±0.6; Sertoli, transplanted=197±31.9, p<0.0001). This asymmetric rotational behavior was indicative of a lesion on the side of the brain which was not transplanted with Sertoli cells. Therefore, Sertoli cell implants, vis-a-vis trophic mechanisms, have neuroprotective and prophylactic effects on subsequent brain lesions. This provides evidence that Sertoli transplantation may also be useful in treating neurodegenerative diseases early, before significant damage is present.

These results, taken together, show that the Sertoli cells ameliorate the behavioral and functional deficits of animal models of Parkinson's disease and Huntington's disease.

The mechanism involved is most likely the secretion of Sertoli cell-derived growth factors, as demonstrated by the sprouting of neuronal tissue as shown in Example 2, and regulatory factors which promote the repair and the prolonged support of the relevant nervous tissue. Additionally, Sertoli cells may protect and promote nervous tissue repair in the brain by inhibiting glial cell activation at the lesion site. These results also demonstrate the viability in situ of transplanted Sertoli cells.

Throughout this application various publications are referenced by citation or number. Full citations for the publication are listed below. The disclosure of these publications in their entireties are hereby incorporated by reference into this application in order to more fully describe the state of the art to which this invention pertains.

The invention has been described in an illustrative manner, and it is to be understood the terminology used is intended to be in the nature of description rather than of limitation.

Obviously, many modifications and variations of the present invention are possible in light of the above teachings. Therefore, it is to be understood that within the scope of the appended claims, the invention may be practiced otherwise than as specifically described.

TABLE 1

I. Sertoli Cell-Derived Growth and Regulatory Factors (Partial List)

| Category and Protein | Function |
| --- | --- |
| Hormones/Growth Factors | |
| Mullerian Inhibiting Substance | inhibits Mullerian duct |
| Inhibin | inhibits FSH release |
| Insulin-like Growth Factor (Sommatomedins A and C, IGF) | growth factor |
| Prodynorphin | |
| Interleukin-1α | mitogen |
| Transforming Growth Factor α & β | growth factors |
| Basic Fibroblast Growth Factor | growth factor |
| LHRH-like Factor (unpurified or incompletely characterized) | Leydig cell steroidogenesis |
| Sertoli Secreted Growth Factor | growth factor |
| Seminiferous Growth Factor | |
| Leydig Cell Stimulatory Activity | |
| Testins | |
| CMB proteins | |
| Vitamin Binding Proteins | vitamin transport |
| Transport and Bioprotection | |
| Transferrin | iron transport |
| Ceruloplasm | copper transport |
| Saposin | binds glycosphingolipids |
| SGP-2 (Clusterin) | lipid transport |
| Androgen Binding Protein | transports T and DHT |
| SPARC | calcium binding protein? |
| IGF Binding Proteins | IGF transport |
| Riboflavin Binding Protein | riboflavin transport |
| Proteases and protease Inhibitors | |
| Plasminogen Activator | protease |
| Cyclic Protein-2 | protease inhibitor |
| Cystatin | protease inhibitor |
| α$_2$-Macroglobulin | protease inhibitor |
| Type IV Collagenase | protease |
| Metalloproteinases | protease |
| Basement membrane | |
| Collagen IV | |
| Laminin | |
| Proteoglycans | |

REFERENCES CITED

Bjorklund and Stenevi, "Intracerebral neural grafting: a historical perspective" in Bjorklund, A and U. Stenevi, eds. *Neural grafting in the mammalian CNS*, Amsterdam: Elsevier, 3–11 (1985).

Bjorklund, "Dopaminergic transplants in experimental Parkinsonism: Cellular mechanisms of graft-induced functional recovery" *Current Biology*, 2:683–689 (1992).

Borlongan et al., "PR: Systemic 3-nitropropionic acid: Behavior deficits and striatal damage in rats" *Brain Research Bulletin*, 36:549–556 (1995).

Cameron et al., "Successful islet/abdominal testis transplantation does not require Leydig cells" *Transplantation*, 50:549–556 (1995).

Cameron and Muffly, "Hormonal regulation of spermatid binding to Sertoli cells in vitro." *J. Cell Sci.*, 100:523–533 (1991).

Griswold, "Protein Secretion by Sertoli cells: general considerations" in Russell, L. d. and M. D. Griswold eds. The Sertoli Cell, Cache River Press, Clearwater, Fla., 195–200 (1992).

Isacson et al., "Graft-induced behavioral recovery in an animal model of Huntington's disease" *Proc. Natl. Acad. Sci*, 83:2728–2732 (1984).

Koutouzis et al., "PR: Systemic 3-nitropropionic acid: Long term effects on locomotor behavior" *Brain Research*, 646:242–246 (1994).

Lindvall et al., "Transplantation in Parkinson's disease: two cases of adrenal medullary grafts to the putamen" *Ann. Neurol.* 22:457–468 (1987).

Lindvall et al., "Grafts of fetal dopamine neurons survive and improve motor function in Parkinson's disease" *Science*, 247:574–577 (1990).

Pakzaban et al., "Increased proportion of Ache-rich zones and improved morphological integration in host striatum of fetal grafts derived from the lateral but not the medial ganglionic eminence" *Exp. Brain Res.*, 97:13–22 (1993).

Sanberg et al., "Cell transplantation for Huntington's disease" R. G. Landes Co., Boca Raton, Fla., pp.19–21 (1994).

Selawry and Cameron, "Sertoli cell-enriched fractions in successful islet cell transplantation" *Cell Transplan.*, 2:123–129 (1993).

Wictorin et al., "Reformation of long axon pathways in adult rat CNS by human forebrain neuroblasts" *Nature*, 347:556–558 (1990).

What is claimed is:

1. A method of generating in situ trophic factors in CNS tissue comprising transplanting allogeneic or syngeneic Sertoli cells into a CNS tissue of a mammal in need of said trophic factors, wherein said Sertoli cells express said trophic factors in situ.

2. A method as set forth in claim 1 wherein the mammal suffers from Parkinson Disease-like stictal lesions in the substantia nigra which affect dolaminercic neurons, said method further including the step of stereotactically injecting syngeneic or allogeneic Sertoli cells at the site of the lesions wherein the action of the secreted trophic factors causes the amelioration of behavioral and motor deficits caused by the disorder motor deficits caused by the disorder, by the action of the secreted trophic factors.

3. A method as set forth in claim 1, wherein the Sertoli cells are porcine Sertoli cells.

4. A method as set forth in claim 1 wherein the mammal suffers from Huntington's Disease-like striatal lesions affecting GABA-ergic neurons, said method further including the step of stereotactically injecting synceneic or allogeneic Sertoli cells at the site of the lesions wherein the action of the secreted trophic factors causes the amelioration of behavioral and motor deficits caused by the disorder ameliorating behavioral and motor deficits caused by the disorder by the action of the secreted trophic factors.

* * * * *